(12) United States Patent
Sembo

(10) Patent No.: US 6,218,416 B1
(45) Date of Patent: Apr. 17, 2001

(54) PESTICIDAL COMPOSITIONS

(75) Inventor: Satoshi Sembo, Takarazuka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/553,561

(22) Filed: Apr. 20, 2000

(30) Foreign Application Priority Data

Apr. 22, 1999 (JP) .................................................. 11-114984

(51) Int. Cl.⁷ .............................. A01N 43/08; A01N 43/50
(52) U.S. Cl. ........................................... 514/389; 514/471
(58) Field of Search ...................................... 514/471, 389

(56) References Cited

U.S. PATENT DOCUMENTS

| 4,176,189 | 11/1979 | Itaya et al. | 424/273 R |
| 5,532,365 | * 7/1996 | Kodata et al. | 544/212 |

FOREIGN PATENT DOCUMENTS 1649845   4/1995   (EP) .

* cited by examiner

*Primary Examiner*—Allen J. Robinson
(74) *Attorney, Agent, or Firm*—Birch, Stewart, Kolasch & Birch, LLP

(57) ABSTRACT

Provided are compositions typically including 1-methyl-2-nitro-3-[(3-tetrahydrofuryl)methyl]guanidine and [2,5-dioxo-3-(2-propynyl)-1-imidazolidinyl]methyl chrysanthemate, as well as a method of controlling pests.

10 Claims, No Drawings

PESTICIDAL COMPOSITIONS

FIELD OF THE INVENTION

The instant invention relates to compositions which may be utilized to control pests.

BACKGROUND OF THE INVENTION

Various compounds and compositions have been utilized to control a pests but such compounds and compositions have failed to provide a effective control of pests.

U.S. Pat. No. 5,532,365 discloses 1-methyl-2-nitro-3-[(3-tetrahydrofuryl)methyl]guanidine as a compound having a control over insects. U.S. Pat. No. 4,176,189 discloses [2,5-dioxo-3-(2-propynyl)-1-imidazolidinyl]methyl chrysanthemate as an active ingredient of insecticides.

SUMMARY OF THE INVENTION

The instant invention provides compositions comprising 1-methyl-2-nitro-3-[(3-tetrahydrofuryl)methyl]guanidine and [2,5-dioxo-3-(2-propynyl)-1-imidazolidinyl]methyl chrysanthemate as active ingredients. Additionally, the instant invention provides methods of controlling pests comprising applying 1-methyl-2-nitro-3-[(3-tetrahydrofuryl)methyl]guanidine and [2,5-dioxo-3-(2-propynyl)-1-imidazolidinyl]methyl chrysanthemate to a pest or a locus where pests inhabit.

DETAILED DESCRIPTION OF THE INVENTION

1-Methyl-2-nitro-3-[(3-tetrahydrofuryl)methyl]guanidine and [2,5-dioxo-3-(2-propynyl)-1-imidazolidinyl]methyl chrysanthemate which are present in the compositions typically act as active ingredients therein. The compositions typically comprise the active ingredients so that the total amount of 1-methyl-2-nitro-3-[(3-tetrahydrofuryl)methyl]guanidine and [2,5-dioxo-3-(2-propynyl)-1-imidazolidinyl]methyl chrysanthemate is from 0.005 to 50% by weight, wherein said percentage by weight is based on the total weight of the provided composition. In this regard, when the compositions are utilized to control pests, the compositions of the instant invention can have the total amount of the active ingredients therein at an amount which effectively controls pests. Further, the compositions typically comprise the active ingredients so that the weight-to-weight ratio of 1-methyl-2-nitro-3-[(3-tetrahydrofuryl)methyl]guanidine to [2,5-dioxo-3-(2-propynyl)-1-imidazolidinyl]methyl chrysanthemate is from 1:99 to 99:1, preferably 1:9 to 9:1, more preferably 3:1 to 1:3. Such weight-to-weight ratios in the compositions can vary, but when said compositions are utilized to control a pest, said compositions generally have a sufficient weight-to-weight ratio of 1-methyl-2-nitro-3-[(3-tetrahydrofuryl)methyl]guanidine to [2,5-dioxo-3-(2-propynyl)- 1-imidazolidinyl]methyl chrysanthemate therein at a rate to provide a synergistic control over pests.

Since the compositions can contain various active isomers of [2,5-dioxo-3-(2-propynyl)-1-imidazolidinyl]methyl chrysanthemate, any active stereoisomer of [2,5-dioxo-3-(2-propynyl)-1-imidazolidinyl]methyl chrysanthemate or mixture thereof can be utilized in the instant invention, if so desired. Examples of stereoisomes of [2,5-dioxo-3-(2-propynyl)-1-imidazolidinyl]methyl chrysanthemate which can be utilized in the instant invention include [2,5-dioxo-3-(2-propynyl-1-imidazolidinyl]methyl (1RS)-cis,trans-chrysanthemate, [2,5-dioxo-3-(2-propynyl)-1-imidazolidinyl]methyl (1R)-cis,trans-chrysanthemate (common name imiprothrin), [2,5-dioxo-3-(2-propynyl)-1-imidazolidinyl]methyl (1R)-trans-chrysanthemate and the like.

The compositions of the instant invention are typically formulated as suitable formulations of 1-methyl-2-nitro-3-[(3-tetrahydrofuryl)methyl]guanidine and [2,5-dioxo-3-(2-propynyl)-1-imidazolidinyl]methyl chrysanthemate. Examples of such formulations of the inventive compositions include liquid formulations, dusts, wettable powders, granules, paste formulations, microencapsulated formulations, foaming formulations, aerosols, liquid carbon dioxide solution formulations, tablets, poison baits, smoking formulations, fogging formulations, sheet formulations, resin formulations and the like. Examples of said liquid formulations of the compositions include emulsifiable concentrates, oil formulations, spot-on formulations, pour-on formulations, shampoo formulations, suspensible concentrates and the like.

Such formulations of the compositions can be produced by well known formulating procedures. For example, a formulation of the instant invention can be produced by mixing together 1-methyl-2-nitro-3-[(3-tetrahydrofuryl)methyl]guanidine and [2,5-dioxo-3-(2-propynyl)-1-imidazolidinyl]methyl chrysanthemate and optionally adding thereto or mixing therewith formulation auxiliaries or carriers. Based on the formulation type of the compositions, said formulations may also be produced by forming said mixture into a suitable form, if so desired. As such, the formulations of the compositions may contain 1-methyl-2-nitro-3-[(3-tetrahydrofuryl)methyl]guanidine and [2,5-dioxo-3-(2-propynyl)-1-imidazolidinyl]methyl chrysanthemate without additional components, but may additionally contain the carrier or formulation auxiliary, if so desired.

Examples of formulation auxiliaries which can be utilized in the compositions include emulsifiers, dispersing agents such as a lignin sulfonate salt and methylcellulose, adhesive agents such as carboxymethylcellulose, gum arabic, polyvinyl alcohol and polyvinyl acetate, coloring agents such as iron oxide, titanium oxide, Persian blue, alizarine dye, azo dye and phthalocyanine dye and the like. Examples of said emulsifiers which can be utilized in the instant invention include ionic emulsifiers such as an alkylsulfonate salt, alkylsulfate salt, alkylarylsulfonate salt and arylsulfonate salt, nonionic emulsifiers such as a polyoxyethylene fatty acid ester, polyoxyethylenealkylaryl ether and polyoxyethylene fatty acid alcohol ether and the like.

The compositions of the instant invention generally utilize therein a carrier selected form a solid carrier, a liquid carrier and a propellant, when present. In such cases in which the compositions additionally contain a carrier, said compositions typically contain the carrier in an amount of from 50% to 99.995%, wherein said percentage by weight is based on the total weight of the provided composition.

Examples of solid carriers which can be utilized in the compositions include gelatin, vaseline, methyl cellulose, lanolin, lard, natural-occurring or synthetic minerals such as clay, kaolin, talc, bentonite, sericite, quartz, sulfur, activated carbon, calcium carbonate, diatomaceous earth, pumice stone, calcite, meerschaum, dolomite, silica, alumina, vermiculite and perlite, fine granules such as granulated sawdust, corncob, coconut shell and tobacco stems and the like.

Examples of liquid carriers which can be utilized in the compositions include liquid paraffins, aromatic or aliphatic hydrocarbons such as xylene, toluene, alkylnaphthalene, phenylxylylethane, kerosene, gas oils, hexane and cyclohexane, halogenated hydocarbons such as chlorobenzene, dicloromethane, dichloroethane and trichloroethane, alcohols such as methanol, ethanol, isopropyl alcohol, butanol, hexanol and ethylene glycol, ethers such as diethyl ether, ethylene glycol dimethyl ether, diethylene glycol monomethyl ether, diethylene glycol monoethyl ether, propylene glycol monomethyl ether, tetrahydrofuran and dioxane, esters such as ethyl acetate and butyl acetate, ketones such as acetone, methyl ethyl ketone, methyl isobutyl ketone and cyclohexanone, nitriles such as acetonitrile and isobutyronitrile, amides such as N,N-dimethylformamide and N,N-dimethylacetamide, botanical oils such as soybean oil and cotton seed oil, botanical essential oils such as orange oil, hyssop oil and lemon oil, water and the like.

Examples of propellants which can be utilized in the compositions include propane gas, butane gas, flon gas, liquified petroleum gas (LPG), dimethyl ether, carbonate gas and the like. By utilizing the propellant in the compositions, the compositions may be formulated into the foaming formulations, aerosols and the like.

When formulating the compositions as poison baits, said poison baits can additionally contain at least one selected from a bait ingredient, anti-oxident, preservative, agent for averting unintentional child or pet ingestion of the poison bait, pest attractant fragrance and the like. Examples of the bait ingredients which can be in said poison baits include powdered crop, botanical oil, sugar, crystallized cellulose and the like. Examples of anti-oxidents which can be in said poison bait include dibutyl hydroxytoulene, nordihydroguaiaretic acid and the like. As an example of a preservative which can be utilized in said poison baits, there is included dehydroacetic acid and the like. As an example of an agent for averting unintentional child or pet ingestion of the poison bait which can be utilized in said poison baits, there is included powdered pepper and the like. Examples of pest attractant fragrances include cheese fragrances, onion fragrances and the like.

When formulating the compositions as resin formulations, said resin formulation can additionally contain resin material such as a polyvinyl chloride or polyurethane. The polyvinyl chloride and polyurethane when utilized in the compositions may optionally have a plasticizer added thereto. Examples of plasticizers which can be utilized in the instant invention include phthalate esters such as dimethyl phthate and dioctyl phthate, adipate esters, stearate esters and the like.

Such resin formulations of the compositions can be formulated by mixing together 1-methyl-2-nitro-3-[(3-tetrahydrofuryl)methyl]guanidine, [2,5-dioxo-3-(2-propynyl)-1-imidazolidinyl]methyl chrysanthemate and said resin material, and forming the resulting mixture to a desired form. For example, the resin formulations may be formulated by mixing together 1-methyl-2-nitro-3-[(3-tetrahydrofuryl)methyl]guanidine, [2,5-dioxo-3-(2-propynyl)- 1-imidazolidinyl]methyl chrysanthemate and said resin material by using a standard kneading machine and then be formed into a desired form by employing a molding process. Examples of known molding processes which can be employed to formulate the resin formulations include ejection molding, extrusion molding, press molding and the like. The resin formulations of the instant invention can be further formed by additional molding or cutting. Examples of such resin formulations of the instant invention include board formulations, film formulations, tape formulations, rope formulations, net formulations, animal collar formulations, animal eartag formulations, sheet formulations, pest attracting rope formulations, wrapping film formulations, gardening pillar formulations and the like.

The compositions of the instant invention may also comprise at least one additional pesticidal ingredient or synergist. Examples of such pesticidal ingredients which may be utilized in the compositions include organophosphorous compounds, carbamate compounds, compounds inhibiting chitin-synthesis in pests, juvenile hormone analogues, N-phenylpyrazole compounds, agents controlling endoparasites of animals, pest repellents and the like. Examples of organophosphorous compounds which may be utilized in the compositions include dichlorvos, tetrachlorovinphos, fenthion, clorpyrifos, diazinon and the like. Examples of carbamate compounds which may be utilized in the compositions include propoxur, carbaryl, metoxadiazone, fenobucarb and the like. Examples of compounds inhibiting chitin-synthesis in pests which may be utilized in the compositions include lufenuron, chlorfluazuron, hexaflumuron, cyromazine, 1-(2,6-difluorobenzoyl)-3-[2-fluoro-4-(1,1,2,3, 3,3-hexafluoropropoxyphenyl] urea and the like. Examples of juvinile hormone analogues which may be utilized in the compositions include pyriproxyfen, methoprene, hydroprene, fenoxycarb and the like. Examples of agents controlling endoparasites of animals which may be utilized in the compositions include milbemycin, abamectine, ivermectin and the like. Examples of pest repellents which may be utilized in the compositions include N,N-diethyl-m-toluamide (DEET), limonin, linuron, citronellal, menthol, menthone, hinokitiol, geraniol, eucalyptol, indoxacarb, carane-3,4-diol and the like. Examples of synergists which may be utilized in the compositions include PBO, S421, MGK 264, IBTA and the like.

When utilizing 1-methyl-2-nitro-3-[(3-tetrahydrofuryl) methyl]guanidine and [2,5-dioxo-3-(2-propynyl)-1-imidazolidinyl]methyl chrysanthemate together to control pests, 1-methyl-2-nitro-3-[(3-tetrahydrofuryl)methyl] guanidine and [2,5-dioxo-3-(2-propynyl)-1-imidazolidinyl] methyl chrysanthemate are typically applied to a pest or a locus of where a control of a pest is desired. As such, 1-methyl-2-nitro-3-[(3-tetrahydrofuryl)methyl]guanidine and [2,5-dioxo-3-(2-propynyl)-1-imidazolidinyl]methyl chrysanthemate may be utilized to control pests by applying the composition to the pest or to a habitat of said pest. Furthermore, 1-methyl-2-nitro-3-[(3-tetrahydrofuryl) methyl]guanidine and [2,5-dioxo-3-(2-propynyl)-1-imidazolidinyl]methyl chrysanthemate may also be utilized to control pests by applying the composition to products in which a control of pests is desired. As such, 1-methyl-2-nitro-3-[(3-tetrahydrofuryl)methyl]guanidine and [2,5-dioxo-3-(2-propynyl)-1-imidazolidinyl]methyl chrysanthemate may be added to electric wire coverings or synthetic resin sheets to provide various pest-proof products.

In utilizing 1-methyl-2-nitro-3-[(3-tetrahydrofuryl) methyl]guanidine and [2,5-dioxo-3-(2-propynyl)-1-imidazolidinyl]methyl chrysanthemate as active ingredients to control pests in the household area, the active ingredients are utilized in a total amount which effectively controls pests. Such a total amount of 1-methyl-2-nitro-3-[(3-tetrahydrofuryl)methyl]guanidine and [2,5-dioxo-3-(2-propynyl)-1-imidazolidinyl]methyl chrysanthemate which effectively controls pests can be an amount of from 0.001 to 100 mg/m$^3$, when such pests encompass household pests and ectoparasites of animals. Examples of such household pests and ectoparasites include flies, mosquitoes, cockroaches, acarina, fleas, lice, termites and the like. In such cases, said emulsifiable concentrates, wettable powders, flowables, microencapsulated formulations and the like are usually diluted so that 1-methyl-2-nitro-3-[(3-tetrahydrofuryl)methyl]guanidine and [2,5-dioxo-3-(2- propynyl)-1-imidazolidinyl]methyl chrysanthemate is at a concentration of from 0.1 to 1,000 ppm. In diluting such formulations of the instant invention, said formulations may be additionally diluted with water, if so desired. Further, said oil formulations, aerosols, fogging formulations, poison baits, sheet formulations and the like usually utilize 1-methyl-2-nitro-3-[(3-tetrahydrofuryl)methyl]guanidine and [2,5-dioxo-3-(2-propynyl)-1-imidazolidinyl]methyl chrysanthemate to control pests without additional dilution.

In controlling pests of wood material such as termites, 1-methyl-2-nitro-3-[(3-tetrahydrofuryl)methyl]guanidine and [2,5-dioxo-3-(2-propynyl)-1-imidazolidinyl]methyl chrysanthemate are typically utilized in a total amount which effectively controls the pests of wood material. In such cases, said active ingredients can be directly applied to the pest, but can also be applied to the soil, wood material, other habitats of the pest of wood material or the like. For example, 1-methyl-2-nitro-3-[(3-tetrahydrofuryl)methyl] guanidine and [2,5-dioxo-3-(2-propynyl)-1-imidazolidinyl] methyl chrysanthemate can be utilized as active ingredients in a total amount of from 0.1 to 10,000 mg/m$^2$, wherein the amount is based on the provided area of the pest habitat. However, it should be noted that such an amount of said active ingredients may vary on the type of the pest of wood material, formulation form, locus of utilizing said active ingredients, method of utilizing said active ingredients or the like. Said active ingredients may also be utilized to control the pests of wood material by adding 1-methyl-2-nitro-3-[(3-tetrahydrofuryl)methyl]guanidine and [2,5-dioxo-3-(2-propynyl)-1-imidazolidinyl]methyl chrysanthemate to produce pest-proof products such as electric wire coverings, synthetic resin sheets and constructed wood material such as veneer and the like. In order to produce the constructed wood material, there are methods which include adding 1-methyl-2-nitro-3-[(3-tetrahydrofuryl)methyl]guanidine and [2,5-dioxo-3-(2-propynyl)-1-imidazolidinyl]methyl chrysanthemate to an adhesive agent and utilizing the resulting adhesive agent to produce the veneer or constructed wood material.

Further, 1-methyl-2-nitro-3-[(3-tetrahydrofuryl)methyl] guanidine and [2,5-dioxo-3-(2-propynyl)-1-imidazolidinyl] methyl chrysanthemate can be utilized as active ingredients to control ectoparasites of domestic animals, with examples of the domestic animals including pets such as dogs and cats, cows, bulls, lambs and the like. When applying said active ingredients to the domestic animal, said active ingredients may be applied in an amount of from 0.1 to 10,000 mg/kg, wherein the amount is based on the weight of the provided domestic animal. When applying said active ingredients to the floor or to outdoor locations, said active ingredients can be applied at an amount of from 0.1 to 10,000 mg/m$^2$, wherein said amount is based on the area of the provided floor or outdoor location.

Furthermore, 1-methyl-2-nitro-3-[(3-tetrahydrofuryl) methyl]guanidine and [2,5-dioxo-3-(2-propynyl)-1-imidazolidinyl]methyl chrysanthemate can be utilized as active ingredients for agricultural purposes. In such cases, said active ingredients are generally utilized in an amount which effectively protects crops in the agricultural field from pests. The amount of the active ingredients which provides the effective protection from the pests is typically an amount of from 1 to 1,000 g/ha, preferably 10 to 300 g/ha, wherein the amount is based on the are of the provided agricultural field. It should be noted that when said active ingredients are utilized for the agricultural purposes, the granule formulations, dusts or the like formulations of the instant invention can be utilized without dilution. However, it should be noted that when the emulsifiable concentrates, suspensible concentrates, wettable powders or the like formulations of the instant invention are utilized for the agricultural purposes, said formulations are typically diluted to a concentration of from 1 to 1,000 ppm, preferably 10 to 200 ppm. In diluting such formulations, water may be utilized to dilute the formulations, if so desired. Such formulations of the instant invention may be utilized for the agricultural purposes by foliar applying said active ingredients to the crops or by applying said active ingredients to the soil in which a control of pests surviving in said soil is desired. Further, the resin formulations of the instant invention, such as a sheet formulation or rope formulation, can be utilized for the agricultural purposes by wrapping the formulation around the crop, by stretching the formulation across a distance which is in the vicinity of a crop, by laying said formulation onto the soil which surrounds the stump of the crop or by the like.

It should also be noted that 1-methyl-2-nitro-3-[(3-tetrahydrofuryl)methyl]guanidine and [2,5-dioxo-3-(2-propynyl)-1-imidazolidinyl]methyl chrysanthemate can be applied together to a locus by employing various methods. For example, as a method of applying 1-methyl-2-nitro-3-[(3-tetrahydrofuryl)methyl]guanidine and [2,5-dioxo-3-(2-propynyl)-1-imidazolidinyl]methyl chrysanthemate, there are mentioned methods which have said active ingredients applied to a locus as a mixture of the instant invention or as separately in a sequential manner. As an example of the latter type of method, one of the active ingredients is applied to a locus and then the other active ingredient is applied to said locus. Such latter type of the methods include applying 1-methyl-2-nitro-3-[(3-tetrahydrofuryl)methyl]guanidine and [2,5-dioxo-3-(2-propynyl)-1-imidazolidinyl]methyl chrysanthemate in a separate but essentially simultaneous manner, wherein the active ingredients are present in separate compositions that are applied to a locus at an essentially simultaneous time or within a essentially simultaneous timeframe.

Pests which are typically controlled by the instant invention typically include nematodes, Arthropods such as flies, mosquitoes, cockroaches, mites, ticks, fleas, lice and termites and the like. More particularly, examples of Arthropods which can be controlled with the instant invention include Hemiptera, Lepidoptera, Diptera, Coleoptera, Cockroaches (Dictyoptera), Thysanoptera, Hymenoptera, Orthoptera, Siphonaptera, Anoplura, termites (Isoptera), Acarina and the like.

Examples of Hemiptera include planthoppers (Delphacidae) such as small brown planthopper (*Laodelphax striatellus*), brown planthopper (*Nilaparvata lugens*) and white-backed rice planthopper (*Sogatella furcifera*), Deltocephalidae such as green rice leafhopper (*Nephotettix cincticeps*) and green rice leafhopper (*Nephotettix virescens*), aphids (Aphididae) such as cotton aphid (*Aphis gossypii*) and green peach aphid (*Myzus persicae*), plant bugs (Heteroptera) such as green stink bug (*Nezara antennata*) and bean bug (*Riptortus clavetus*), whiteflies (Aleyrodidae) such as greenhouse whitefly (*Trialeurodes vaporariorum*) and silver leaf whitefly (*Bemisia argentifolii*), scales such as red scale (*Aonidiella aurantii*), San Jose scale (*Comstockaspis perniciosa*), citrus snow scale (*Unaspis citri*), red wax scale (*Ceroplastes rubens*) and cottonycushion scale (*Icerya purchasi*), lace bugs (Tingidae), jumping plantlice (Psyllidae) and the like.

Examples of Lepidoptera include pyralid moths (Pyralidae) such as rice stem borer (*Chilo suppressalis*), rice leafroller (*Cnaphalocrocis medinalis*), cotton leafroller (*Notarcha derogata*) and Indian meal moth (*Plodia interpunctella*), owlet moths (Noctuidae) such as tobacco cutworm (*Spodoptera litura*), rice armyworm (*Pseudaletia separata*), Trichoplusia spp., Heliothis spp. and Helicoverpa spp., whites (Pieridae) such as common cabbageworm (*Pieris rapae*), totricids (Tortricidae) such as Adoxophyes spp., oriental fruit moth (*Grapholita molesta*) and *Cydia pomonella*, Carposinidae such as peach fruit moth (*Carposina niponensis*), lyonetiid moths (Lyonetiidae) such as Lyonetia spp., tussock moths (Lymantriidae) such as Lymantria spp. and *Euproctis spp.*, yponomeutids (Yponomeutidae) such as diamondback moth (*Plutella xylostella*), gelechiid moths (Gelechiidae) such as pink bollworm (*Pectinophora gossypiella*), tiger moths (Arctiidae) such as fall webworm (*Hyphantia cunea*), clothes moths (Tineidae) such as casemaking clothes moth (*Tinea translucens*) and webbing clothes moth (*Tineola bisselliella*) and the like.

Examples of Diptera include Anopheles spp. such as *Anopheles sinensis*, mosquitoes (Culicidae) such as common mosquito (*Culex pipiens pallens*), *Culex tritaeniorhynchus* and *Culex quinquefasciatus*, Aedes spp. such as yellow fever mosquito (*Aedes aegypti*) and *Aedes albopictus*, muscid flies (Muscidae) such as housefly (*Musca domestica*) and false housefly (*Muscina stabulans*), Anthomyiidae such as seedcorn maggot (*Delia platura*) and onion maggot (*Delia antiqua*), midges (Chironomidae), blow flies (Calliphoridae), flesh flies (Sarcophagidae), little housefly (*Fannia canicularis*), fruit flies (Tephritidae), vinegar flies (Drosophilidae), moth flies (Psychodidae), black flies (Simuliidae), breeze flies (Tabanidae), stable flies (Stomoxyidae), leaf miner flies (Agromyzidae) and the like.

Examples of Coleoptera include Epilachna spp. such as twenty-eight-spotted ladybird (*Epilachna vigintioctopunctata*), corn rootworms such as western corn rootworm (*Diabrotica virgifera virgifera*) and southern corn rootworm (*Diabrotica undecimpunctata howardi*), scarabs (Scarabaeidae) such as cupreous chafer (*Anomala cuprea*) and soybean beetle (*Anomala rufocuprea*), weevils (Curculionidae) such as maize weevil (*Sitophilus zeamais*), ricewater weevil (*Lissorhoptrus oryzophilus*) and adzuki bean weevil (*Callosobruchuys chienensis*), darkling beetles (Tenebrionidae) such as yellow mealworm (*Tenebrio molitor*) and red flour beetle (*tribolium castaneum*), leaf beetles (Chrysomelidae) such as cucurbit leaf beetle (*Aulacophora femoralis*), striped flea beetle (*Phyllotreta striolata*) and Colorado potato beetle (*Leptinotarsa decemlineata*), deathwatch beetles (Anobiidae), powderpost beetles (Lyctidae), false powderpost beetles (Bostrychidae), longicorn beetles (Cerambycidae), robe beetles (*Paederus fuscipes*) and the like.

Examples of Dictyoptera include German cockroach (*Blattella gernanica*), smokybrown cockroach (*Periplaneta fulginosa*), American cockroach (*Periplaneta americana*), brown cockroach (*Periplaneta brunnea*), oriental cockroach (*Blatta orientalis*) and the like.

Examples of Thysanoptera include *Thrips palmi*, onion thrips (*Thrips tabaci*) and the like.

Examples of Hymenoptera include ants (Formicidae), hornets (Vespidae), bethylid wasps (Bethylidae), sawflies (Tenthredinidae) such as cabbage sawfly (*Athalia japonica*) and the like.

Examples of Orthoptera include mole crickets (Gryllotalpidae), grasshoppers (Acrididae) and the like.

Examples of Siphonaptera include cat flea (*Ctenocephalides felis*), dog flea (*Ctenocephalides canis*), human flea (*Pulex irritans*), oriental rat flea (*Xenopsylla cheopis*) and the like.

Examples of Anoplura include *Pediculus humanus corporis*, crab louse (*Phthirus pubis*), *Haematopinus eurysternus, Dalmalinia ovis* and the like.

Examples of Isoptera include *Reticulitermes speratus*, Formosan subterranean termite (*Coptotermes formosanus*) and the like.

Examples of Acarina include eriophyid mites (Eriophyidae) such as pink citrus rust mite (*Aculops pelekassi*), tarsonemid mites (Tarsonemidae) such as broad mite (*Polyphagotarsonemus latus*), acarid mites (Acaridae) such as mold mite (*Tyrophagus putrescentiae*), spider mites (Tetranychidae) such as carmine spider mite (*Tetranychus urticae*), citrus red mite (*Panonychus citri*) and *Oligonychus spp.*, lxodidae such as *Haemaphysalis longicornis, Haemaphysalis flava, Dermacentor taiwanicus, Ixodes ovatus, Ixodes persulcatus and Boophilus microplus*, Dermanyssidae such as American house dust mite (*Dennatophagoides farinae*) and *Dermatophagoides ptrenyssnus*, Cheyletidae such as *Cheyletus eruditus, Cheyletus malaccensis* and *Cheyletus moorei*, false spider mites (Tenuipalpidae), Tuckerellidae, chicken mites (*Dernanyssus gallinae*) and the like.

Examples of Nematoda include coffee root-lesion nematode (*Pratylenchus coffeae*), *Pratylenchus fallax*, soybean cyst nematode (*Heterodera glycines*), potato cyst nematode (*Globodera rostochiensis*), northern root-knot nematode (*Meloidogyne hapla*) and the like.

EXAMPLES

Formulation Example 1 (Emulsifiable concentrate)

Two and one-half (2.5) parts by weight of *1*-methyl-2-nitro-3-[(3-tetrahydrofuryl)methyl]guanidine, 2.5 parts by weight of [2,5-dioxo-3-(2-propynl)1-imidazolidinyl]methyl (1R)-cis,trans chrysanthemate (common name: imiprothrin), 30 parts by weight of isopropyl alcohol, 8 parts by weight of polyoxyethylenealkylaryl ether, 2 parts by weight of sodium alkylarylsulfonate and 85 parts by weight of xylene are mixed together to formulate an emulsifiable concentrate formulation of the instant invention.

Formulation Example 2 (Aerosol)

One-tenth (0.1) part by weight of 1-methyl-2-nitro-3-[(3-tetrahydrofuryl)methyl]guanidine, 0.1 parts by weight of [2,5-dioxo-3-(2-propynyl)-1-imidazolidinyl]methyl (1R)-cis,trans chrysanthemate (common name: imiprothrin), 30 parts by weight of isopropyl alcohol and 29.8 parts by weight of distilled water are mixed together, are dissolved and are placed in an aerosol container. A valve component is connected onto the aerosol container and 40 parts by weight of liquified petroleum gas (LPG) is packed into the aerosol container, to formulate a water-based aerosol of the instant invention.

Formulation Example 3 (Fogging formulation)

Five (5) parts by weight of *1*-methyl-2-nitro-3-[(3-tetrahydrofuryl)methyl]guanidine, 5 parts by weight of [2,5-dioxo-3-(2-propynyl)-1-imidazolidinyl]methyl (1R)-cis, trans chrysanthemate (common name: imiprothrin), 7 parts by weight of ethyl oleate, 0.5 parts by weight of zinc oxide and 2 parts by weight of α-starch are mixed together in a foaming agent to an amount of 100 parts by weight. Water is added to the mixture. Subsequently, the mixture is kneaded, is formed into granules with an extrusion machine and is allowed to dry. In a container sectioned by an aluminum wall divider, 2 grams of said granules are placed into one section thereof and 50 grams of magnesium oxide are placed into the other section thereof, to formulate a fogging formulation.

Test Example 1

Diethylene glycol monoethyl ether solutions either containing 0.4% weight by volume (w/v) of 1-methyl-2-nitro-3-[(3-tetrahydrofuryl)methyl]guanidine or 0.4% weight by volume (w/v) of [2,5-dioxo-3-(2-propynyl)-1-imidazolidinyl]methyl (1R)-cis,trans chrysanthemate (common name: imiprothrin) were produced. Solutions were prepared by mixing together, respectively, the solutions containing 1-methyl-2-nitro-3-[(3-tetrahydrofuryl)methyl]guanidine and the solutions containing [2,5-dioxo-3-(2-propynyl)-1-imidazolidinyl]methyl (1R)-cis,trans chrysanthemate at ratios of 1:3, 1:1 and 3:1, as provided in Table 1. The solutions and the prepared solution mixtures were diluted with appropriate amounts of distilled water. In the diluted solutions, the concentrations in weight by volume (w/v) of 1-methyl-2-nitro-3-[(3-tetrahydrofuryl)methyl]guanidine therein corresponding to [2,5-dioxo-3-(2-propynyl)-imidazolidinyl]methyl (1R)-cis,trans chrysanthemate therein were 0.1/0, 0.2/0, 0.15/0.05, 0.1/0.1, 0.05/0.15, 0/0.1 and 0/0.2, as provided in Table 1.

Triangular column shaped wooden containers containing 5 male and 5 female German cockroaches (*Blattela germanica*) therein were placed, respectively, upright in the central region of cubic glass boxes which posses a volume of 0.34 m$^3$ and a side length of 70 cm, and in which said triangular column shaped wooden container possesses a substantially equilateral triangle base, a side length of 3.5 cm and a height of 15 cm. Four and one-fifth milliliters (4.2 mL) of the prepared solutions were sprayed, respectively, into the glass boxes with a spray gun. Ten (10) minutes after spraying the compositions, the cockroaches were transferred, respectively, to sanitary containers and were provided with water and food. The mortality rates of the cockroaches were observed 1 day thereafter. The results are shown in Table 1.

TABLE 1

| Compound A*/Compound B** | | Cockroach mortality |
|---|---|---|
| mixing ratio | concentration (% w/v) | rate (%) |
| 100:00 | 0.1/0 | 30.0 |
| 100:00 | 0.2/0 | 40.0 |
| 75:25 | 0.15/0.05 | 100.0 |
| 50:50 | 0.1/0.1 | 100.0 |
| 25:75 | 0.05/0.15 | 100.0 |
| 0:100 | 0/0.1 | 10.0 |
| 0:100 | 0/0.2 | 60.0 |

*Compound A represents 1-methyl-2-nitro-3-[(3-tetrahydrofuryl)methyl]guanidine
**Compound B represents [2,5-dioxo-3-(2-propynyl)-1-imidazolidinyl]methyl (1R)-cis,trans chrysanthemate Comparative Example 1

Comparative Example 1 was conducted similar to the procedure provided in Test Example 1, but utilized 2-(4-ethoxyphenyl-2-methylpropyl 3-phenoxybenzyl ether (common name: etofenprox) in place of [2,5-dioxo-3-(2-propynyl)-1-imidazolidinyl]methyl (1R)-cis,trans chrysanthemate. The results are shown in Table 2.

TABLE 2

| Compound A*/Compound C** | | Cockroach Mortality |
|---|---|---|
| mixing ratio | Concentration (% w/v) | Rate (%) |
| 100:00 | 0.1/0 | 30.0 |
| 100:00 | 0.2/0 | 40.0 |
| 75:25 | 0.15/0.05 | 60.0 |
| 50:50 | 0.1/0.1 | 75.0 |
| 25:75 | 0.05/0.15 | 75.0 |
| 0:100 | 0/0.1 | 5.0 |
| 0:100 | 0/0.2 | 30.0 |

*Compound A represents 1-methyl-2-nitro-3-[(3-tetrahydrofuryl)methyl]guanidine
**Compound C represents 2-(4-ethoxyphenyl-2-methylpropyl 3-phenoxybenzyl ether The above test results from the Comparative Example evidence that a composition containing 1-methyl-2-nitro-3-[(3-tetrahydrofuryl)methyl]guanidine and 2-(4-ethoxyphenyl-2-methylpropyl 3-phenoxybenzyl ether therein does not provide a synergistic control over cockroaches.

What is claimed is:

1. A pesticidal composition comprising synergistically effective pest controlling amounts of 1-methyl-2-nitro-3-((3-tetrahydrofuryl)methyl)guanidine and (2,5-dioxo-3-(2-propynyl)-1-imidazolidinyl)methyl chrysanthemate.

2. A pesticidal composition according to claim 1, wherein the weight-to-weight ratio of 1-methyl-2-nitro-3-[(3-tetrahydrofuryl)methyl]guanidine to [2,5-dioxo-3-(2-propynyl)-1-imidazolidinyl]methyl chrysanthemate is from 99:1 to 1:99.

3. A pesticidal composition according to claim 1, wherein the weight-to-weight ratio of 1-methyl-2-nitro-3-[(3-tetrahydrofuryl)methyl]guanidine to [2,5-dioxo-3-(2-propynyl)-1-imidazolidinyl]methyl chrysanthemate is from 9:1 to 1:9.

4. A pesticidal composition according to claim 1, wherein the weight-to-weight ratio of 1-methyl-2-nitro-3-[(3-tetrahydrofuryl)methyl]guanidine to [2,5-dioxo-3-(2-propynyl)-1midazolidinyl]methyl chrysanthemate is from 3:1 to 1:3.

5. A method of controlling pests, the method comprising applying synergistically effective pest controlling amounts of 1-methyl-2-nitro-3-((3-tetrahydrofuryl)methyl)guanidine and (2,5-dioxo-3-(2-propynyl)-1-imidazolidinyl)methyl chrysanthemate to the pest or a locus of where a control of a pest is desired.

6. A method according to claim 5, wherein the locus of where a control of a pest is desired is at least one chosen from a habitat of the pest, foliage of the pest, foliage of crops, soil of agricultural fields and a domestic animal.

7. A method according to claim 5, wherein the weight-to weight ratio of 1-methyl-2-nitro-3-[(3-tetrahydrofuryl)methyl]guanidine to [2,5-dioxo-3-(2-propynyl)-1-imidazolidinyl]methyl chrysanthemate is from 99:1 to 1:99.

8. A method according to claim 5, wherein the weight-to weight ratio of 1-methyl-2-nitro-3-[(3-tetrahydrofuryl)methyl]guanidine to [2,5-dioxo-3-(2-propynyl)-1-imidazolidinyl]methyl chrysanthemate is from 9:1 to 1:9.

9. A method according to claim 5, wherein the weight-to weight ratio of 1-methyl-2-nitro-3-[(3-tetrahydrofuryl)methyl]guanidine to [2,5-dioxo-3-(2-propynyl)-1-imidazolidinyl]methyl chrysanthemate is from 3:1 to 1:3.

10. A method according to claim 7, wherein the pest is a cockroach.

* * * * *